United States Patent
Becker et al.

(10) Patent No.: US 10,537,660 B2
(45) Date of Patent: *Jan. 21, 2020

(54) RESORBABLE, AMINO ACID-BASED POLY(ESTER UREA)S SCAFFOLD FOR VASCULAR GRAFT TISSUE ENGINEERING

(71) Applicant: The University of Akron, Akron, OH (US)

(72) Inventors: Matthew Becker, Stow, OH (US); Darrell Reneker, Akron, OH (US); Yaohua Gao, Akron, OH (US)

(73) Assignee: THE UNIVERSITY OF AKRON, Akron, OH (US)

( * ) Notice: Subject to any disclaimer, the term of this patent is extended or adjusted under 35 U.S.C. 154(b) by 854 days.

This patent is subject to a terminal disclaimer.

(21) Appl. No.: 15/032,809

(22) PCT Filed: Oct. 29, 2014

(86) PCT No.: PCT/US2014/062888
§ 371 (c)(1),
(2) Date: Apr. 28, 2016

(87) PCT Pub. No.: WO2015/066173
PCT Pub. Date: May 7, 2015

(65) Prior Publication Data
US 2016/0250382 A1    Sep. 1, 2016

Related U.S. Application Data

(60) Provisional application No. 61/896,687, filed on Oct. 29, 2013.

(51) Int. Cl.
*A61L 27/18*      (2006.01)
*A61L 27/58*      (2006.01)
(Continued)

(52) U.S. Cl.
CPC ............ *A61L 27/18* (2013.01); *A61F 2/07* (2013.01); *A61F 2/82* (2013.01); *A61L 27/58* (2013.01);
(Continued)

(58) Field of Classification Search
USPC ......................................................... 523/113
See application file for complete search history.

(56) References Cited

U.S. PATENT DOCUMENTS 6,971,813 B2 * 12/2005 Shekalim ................ A61L 31/10
118/227
9,745,414 B2 * 8/2017 Becker ................ C08G 63/685
(Continued)

FOREIGN PATENT DOCUMENTS

GB         2130521         6/1984

*Primary Examiner* — Tae H Yoon
(74) *Attorney, Agent, or Firm* — Renner Kenner Greive Bobak Taylor & Weber

(57) ABSTRACT

Embodiments relate to amino acid-based poly(ester urea)s with amino acid residues selected L-leucine, L-isoleucine, L-valine or combinations thereof. The amino acid-based poly(ester urea)S may optionally include a second amino acid residue selected from proteinogenic amino acids and non-proteinogenic amino acids. The amino acid-based poly (ester urea)s are particular useful for the preparation of vascular grafts. Due to the biocompatibility of the amino acid-based poly(ester urea)s, vascular grafts prepared from amino acid-based poly(ester urea)s with small internal diameters (i.e. less than 5 mm) may be prepared and inserted into a patient or animal, and provide a substantial decrease in the risk of failure compared to conventional polymers used in vascular grafts.

11 Claims, 10 Drawing Sheets

(51) Int. Cl.
  *C08G 71/02* (2006.01)
  *A61F 2/07* (2013.01)
  *D01D 5/00* (2006.01)
  *D01F 6/68* (2006.01)
  *D01F 6/84* (2006.01)
  *A61F 2/82* (2013.01)

(52) U.S. Cl.
  CPC ............ *C08G 71/02* (2013.01); *D01D 5/003* (2013.01); *D01F 6/68* (2013.01); *D01F 6/84* (2013.01); *A61F 2230/0069* (2013.01); *C08G 2230/00* (2013.01)

(56) References Cited

U.S. PATENT DOCUMENTS

| | | |
|---|---|---|
| 2004/0063606 A1 | 4/2004 | Chu et al. |
| 2006/0115449 A1 | 6/2006 | Pacetti |
| 2007/0128250 A1 | 6/2007 | Katsarava et al. |
| 2009/0018643 A1 | 1/2009 | Hashi et al. |
| 2009/0253809 A1* | 10/2009 | Gomurashvili ........ A61K 31/74 514/773 |
| 2010/0331957 A1 | 12/2010 | Hashi et al. |
| 2013/0203168 A1* | 8/2013 | Cooper ................. A61L 27/18 435/402 |

* cited by examiner

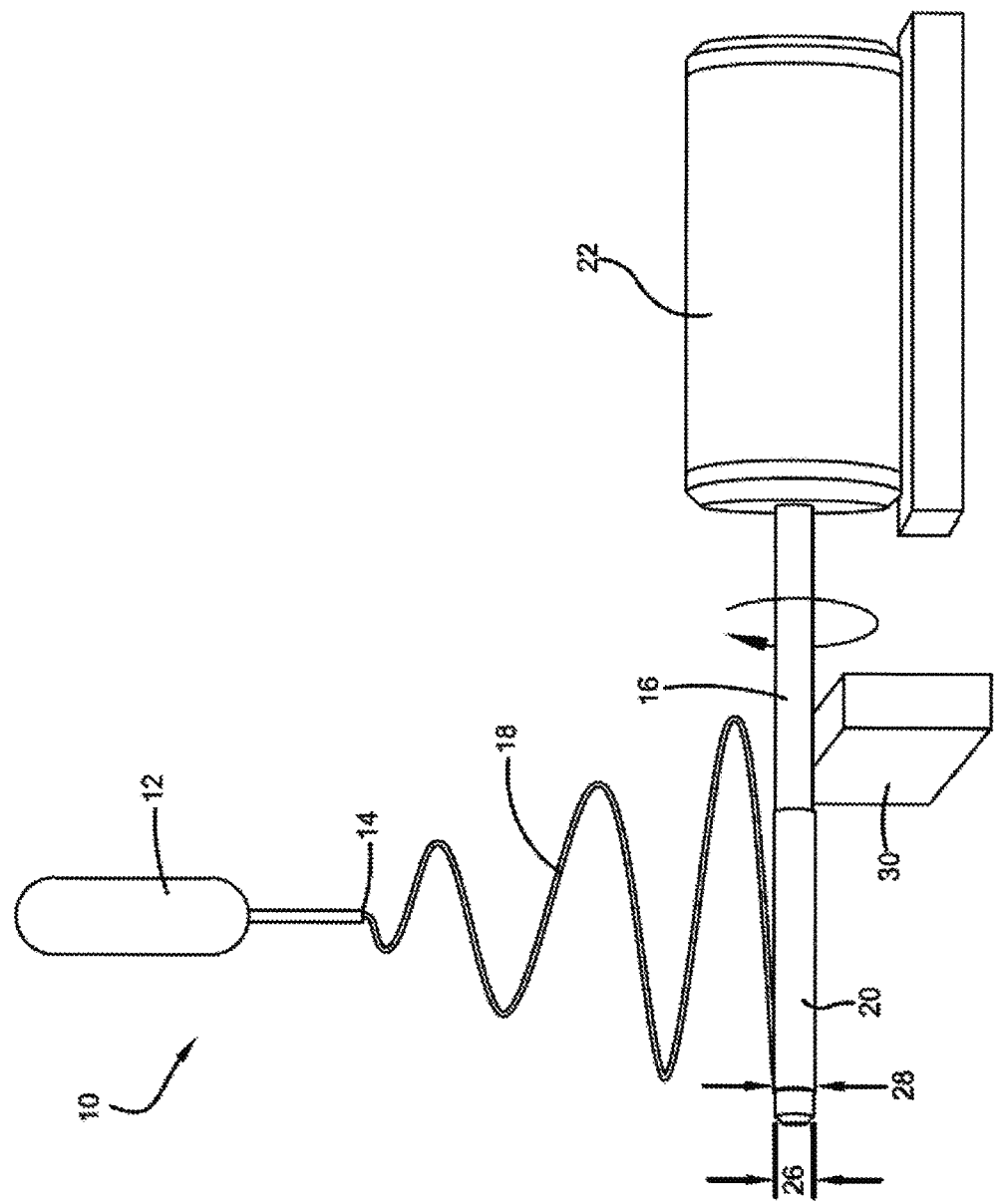

RESORBABLE, AMINO ACID-BASED POLY(ESTER UREA)S SCAFFOLD FOR VASCULAR GRAFT TISSUE ENGINEERING

CROSS-REFERENCE TO RELATED APPLICATIONS

This application claims priority from International application number PCT/US2014/062888, entitled "Resorbable, Amino Acid-Based Poly(Ester Urea)s Scaffold for Vascular Graft Tissue Engineering" filed Oct. 29, 2014 and U.S. Provisional Patent Application No. 61/896,687 filed on Oct. 29, 2013, the contents of which are incorporated herein by reference.

FIELD OF THE INVENTION

One or more embodiments relate to an amino acid-based poly(ester urea) that includes amino acids selected from L-leucine, L-isoleucine, L-valine or combinations thereof. Certain embodiments relate to the methods of preparing or the use of amino acid-based poly(ester urea) that includes amino acids selected from L-leucine, L-isoleucine, L-valine or combinations thereof in a scaffold for a vascular graft.

BACKGROUND OF THE INVENTION

Over the last few decades, biodegradable polymers have been applied to a number of applications in drug delivery and regenerative medicine. While naturally derived biodegradable polymers have distinct bioactivity and cell binding properties, they are difficult to isolate, derivatize and purify. Synthetic polymers also have the potential for immunogenic responses. Synthetic biodegradable polymers have a number of advantages over natural materials, especially the chemical diversity of monomers that can be utilized to tailor the chemical, mechanical and degradation properties of the polymer. There are a number of biodegradable polymers including poly(ε-caprolactone) (PCL), poly(lactic acid) (PLA), poly(glycolide) (PGA), and copolymers thereof that are used clinically and while their properties in vitro and in vivo are largely understood, their range of physical and chemical properties is somewhat limited. Efforts have been made to diversify the pool of synthetic polymers to meet design criteria for more advanced applications.

Currently available vascular grafts fail at small diameters (for example diameters below 5 mm) as a result of acute thrombotic occlusions or chronic anastomic hyperplasia. The failure of small diameter vascular grafts may be traced to the lack of functional intimacy, surface property mis-match, compliance mismatch and microstructure mis-match as a result of the use of polyesters such as polyethylene terephthalate or expanded polytetrafluoroethylene.

Presently there is a need to produce vascular grafts from polymers that have some or all of the following properties biodegradability, resorbable non-toxic hydrolysis byproducts, tunable mechanic properties, synthetic flexibility, and the ability to add functional groups.

SUMMARY OF THE INVENTION

A first embodiment provides an amino acid-based poly(ester urea) comprising an amino acid residue selected from L-leucine, L-isoleucine, L-valine or combinations thereof; and a hydrocarbylene group; where the hydrocarbylene group is attached to the amino acid residue through an ester group.

A second embodiment provides an amino acid-based poly(ester urea) as in the first embodiment, where the amino acid-based poly(ester urea) further includes a second amino acid residue selected from proteinogenic amino acids and non-proteinogenic amino acids.

A third embodiment provides an amino acid-based poly(ester urea) as in the either the first or second embodiment, where the second amino acid residue is defined by the formula:

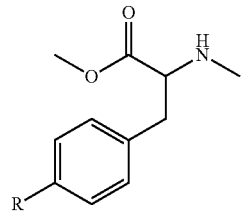

where R is a pendent functional group.

A forth embodiment provides an amino acid-based poly(ester urea) as in any of the first through third embodiments, where the pendent functional group is an oxygen atom connected to a alkyl or aryl group containing an alkyne group, an alkene group, an azide group, a benzyl protected phenol group, a ketone group or a strained cyclooctyne.

A fifth embodiment provides an amino acid-based poly(ester urea) as in any of the first through forth embodiments, where the amino acid-based poly(ester urea) comprises the following formula:

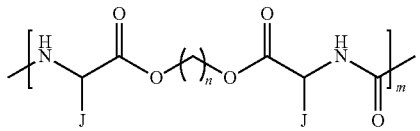

where each J is individually a L-leucine, L-isoleucine, or L-valine side chain, n is about 1 to 20 units, and m is about 10 to 500 units.

A sixth embodiment provides an amino acid-based poly(ester urea) as in any of the first through fifth embodiments, where n is 10 to 12 units.

A seventh embodiment provides an amino acid-based poly(ester urea) as in any of the first through sixth embodiments, where the amino acid-based poly(ester urea) comprises the following formula:

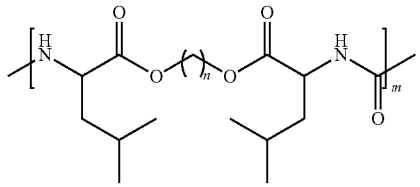

where n is about 1 to 20 units, and m is about 10 to 500 units.

An eighth embodiment provides amino acid-based poly(ester urea) as in any of the first through seventh embodiments, where the amino acid-based poly(ester urea) comprises the following formula:

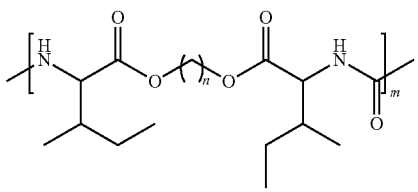

where n is about 1 to 20 units, and m is about 10 to 500 units.

A ninth embodiment provides an amino acid-based poly(ester urea) as in any of the first through eighth embodiments, where the amino acid-based poly(ester urea) comprises the following formula:

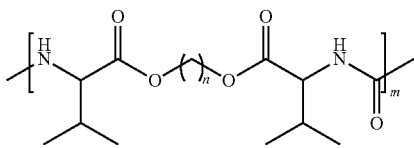

where n is about 1 to 12 units, and m is about 10 to 500 units.

A tenth embodiment provides an amino acid-based poly(ester urea) as in any of the first through ninth embodiments, where the amino acid-based poly(ester urea) comprises the following formula:

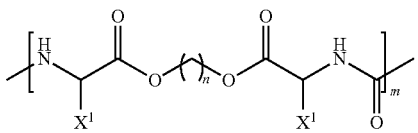

where each $X^1$ is individually an L-leucine, L-isoleucine, L-valine, proteinogenic amino acids or non-proteinogenic amino acid side chain with the proviso that at least one $X^1$ is selected from L-leucine, L-isoleucine, or L-valine, n is 1 to about 20 units, and m is about 10 to 500 units An eleventh embodiment provides an amino acid-based poly(ester urea) as in any of the first through tenth embodiments, where the amino acid-based poly(ester urea) comprises the following formula:

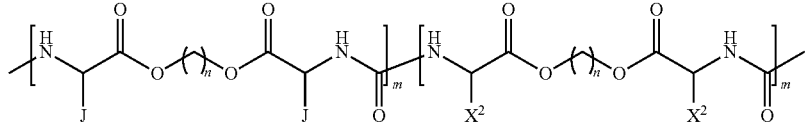

where each J is individually a L-leucine, L-isoleucine, or L-valine side chain, each $X^2$ is individually a proteinogenic amino acids or non-proteinogenic amino acid side chain, each n is individually about 1 to 20 units, and each m is individually about 10 to 500 units A twelfth embodiment provides an amino acid-based poly(ester urea) as in any of the first through eleventh embodiments, where one or more of the $X^1$ or $X^2$ groups is a proteinogenic amino acids or non-proteinogenic amino acid side chain defined by the formula

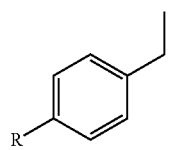

where R is a pendent functional group.

A thirteenth embodiment provides an amino acid-based poly(ester urea) vascular graft comprising a tubular structure comprising an amino acid-based poly(ester urea) with amino acid residues selected from L-leucine, L-isoleucine, L-valine or combinations thereof.

A fourteenth embodiment provides a poly(ester urea) vascular graft as in the thirteenth embodiment, where the amino acid-based poly(ester urea) is defined by the following formula:

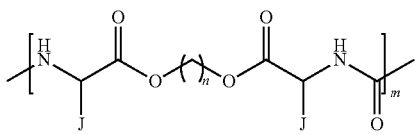

where each J is individually a L-leucine, L-isoleucine, or L-valine side chain, n is about 1 to 20 units, and m is about 10 to 500 units.

A fifteenth embodiment provides a poly(ester urea) vascular graft as in the thirteenth or fourteenth embodiments, where the amino acid-based poly(ester urea) is defined by the following formula:

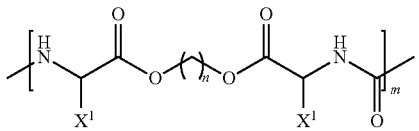

where each $X^1$ is individually an L-leucine, L-isoleucine, L-valine, proteinogenic amino acid or non-proteinogenic amino acid side chain with the proviso that at least one $X^1$ is selected from L-leucine, L-isoleucine, or L-valine, n is 1 to about 20 units, and m is about 10 to 500 units A sixteenth embodiment provides a poly(ester urea) vascular graft as in any of the thirteenth through fifteenth embodiments, where the poly(ester urea) is electrospun.

A seventeenth embodiment provides a poly(ester urea) vascular graft as in any of the thirteenth through sixteenth embodiments, where the vascular graft has an internal diameter of about 0.5 mm to about 20 mm.

An eighteenth embodiment provides a poly(ester urea) vascular graft as in any of the thirteenth through seventeenth embodiments, where the vascular graft has an internal diameter of less than 5 mm.

A nineteenth embodiment provides a poly(ester urea) vascular graft as in any of the thirteenth through eighteenth embodiments, where the vascular graft has a length of about 0.5 cm to about 5 cm.

A twentieth embodiment provides a poly(ester urea) vascular graft as in any of the thirteenth through nineteenth embodiments, where the vascular graft has a wall thickness of about 0.05 mm to about 0.5 mm.

A twenty-first embodiment provides a method of preparing an amino acid-based poly(ester urea) vascular graft comprising (i) providing a charged solution of amino acid-based poly(ester urea) with amino acid residues selected L-leucine, L-isoleucine, L-valine or combinations thereof; (ii) providing a grounded mandrel coated with a dissolvable coating; (iii) electrospinning the poly(ester urea) onto the dissolvable coating of the grounded mandrel to produce a tubular structure, (iv) dissolving the dissolvable coating; and (v) removing the tubular structure from the mandrel.

A twenty-second embodiment provides a method of preparing an amino acid-based poly(ester urea) vascular graft as in the twenty-first embodiment, where the amino acid-based poly(ester urea) defined by the following formula:

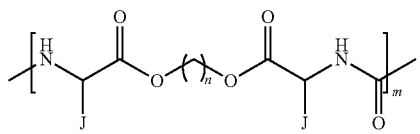

where each J is individually a L-leucine, L-isoleucine, or L-valine side chain, n is about 1 to 20 units, and m is about 10 to 500 units.

A twenty-third embodiment provides a method of preparing an amino acid-based poly(ester urea) vascular graft as in the twenty-first or twenty-second embodiments, where the amino acid-based poly(ester urea) defined by the following formula

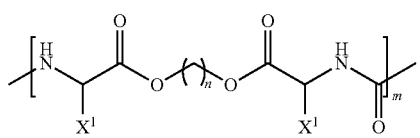

where each $X^1$ is individually an L-leucine, L-isoleucine, L-valine, proteinogenic amino acids or non-proteinogenic amino acid side chain with the proviso that at least one $X^1$ is selected from L-leucine, L-isoleucine, or L-valine, n is 1 to about 20 units, and m is about 10 to 500 units A twenty-fourth embodiment provides a method of preparing an amino acid-based poly(ester urea) vascular graft as in any of the twenty-first through twenty-third embodiments, where the mandrel is rotated during the electrospinning step, and the rotation rate is about 20 rpm to about 5000 rpm.

A twenty-fifth embodiment provides a method of preparing an amino acid-based poly(ester urea) vascular graft as in any of the twenty-first through twenty-fourth embodiments, where the dissolvable coating is a water soluble sugar.

A twenty-sixth embodiment provides a method of preparing an amino acid-based poly(ester urea) vascular graft as in any of the twenty-first through twenty-fifth embodiments, where the mandrel has a total diameter of about 0.5 mm to about 100 mm.

A twenty-seventh embodiment provides a method of preparing an amino acid-based poly(ester urea) vascular graft as in any of the twenty-first through twenty-sixth embodiments, where the mandrel has a total diameter of less than 5 mm.

A twenty-eighth embodiment provides an amino acid-based poly(ester urea) preparable by (i) reacting amino acids with a diol to produce an amino acid-based monomer, where the amino acids are selected from L-leucine, L-isoleucine, L-valine, proteinogenic amino acids, non-proteinogenic amino acids, and a combination thereof, with the proviso that at least one amino acid is selected from L-leucine, L-isoleucine, or L-valine; and (ii) reacting the amino acid-based monomer with a phosgene or triphosgene to produce an amino acid-based poly(ester urea).

A twenty-ninth embodiment provides an amino acid-based poly(ester urea) as in the twenty-eighth embodiment, where the amino acids are selected L-leucine, L-isoleucine, L-valine, and a combination thereof.

A thirtieth embodiment provides an amino acid-based poly(ester urea) as in the twenty-eighth or twenty-ninth embodiments, where the diol is selected from methylene glycol, ethylene glycol, propane-1,3-diol, propane-1,2-diol, butane-1,4-diol, (2-methyl)butane-1,4-diol, pentane-1,5-diol, decane-1,10-diol, undecane-1,11-diol, dodecane-1,12-diol, tridecane-1,13-diol, tetradecane-1,14-diol, pentadecane-1,15-diol, hexadecane-1,16-diol, heptadecane-1,17-diol, octadecane-1,18-diol, nonadecane-1,19-diol, and eicosane-1,20-diol.

A thirty-first embodiment provides an amino acid-based poly(ester urea) as in any of the twenty-eighth through thirtieth embodiments, where the diol is selected from decane-1,10-diol, undecane-1,11-diol, and dodecane-1,12-diol.

BRIEF DESCRIPTION OF THE DRAWINGS

FIG. 2C provides an SEM image of the cross-section (×2.5 K magnification) of a PEU based small diameter vascular graft.

FIG. 7 provides an electrospining apparatus for the production of vascular grafts according to one or more embodiments.

DETAILED DESCRIPTION OF ILLUSTRATIVE EMBODIMENTS

Figure 1:
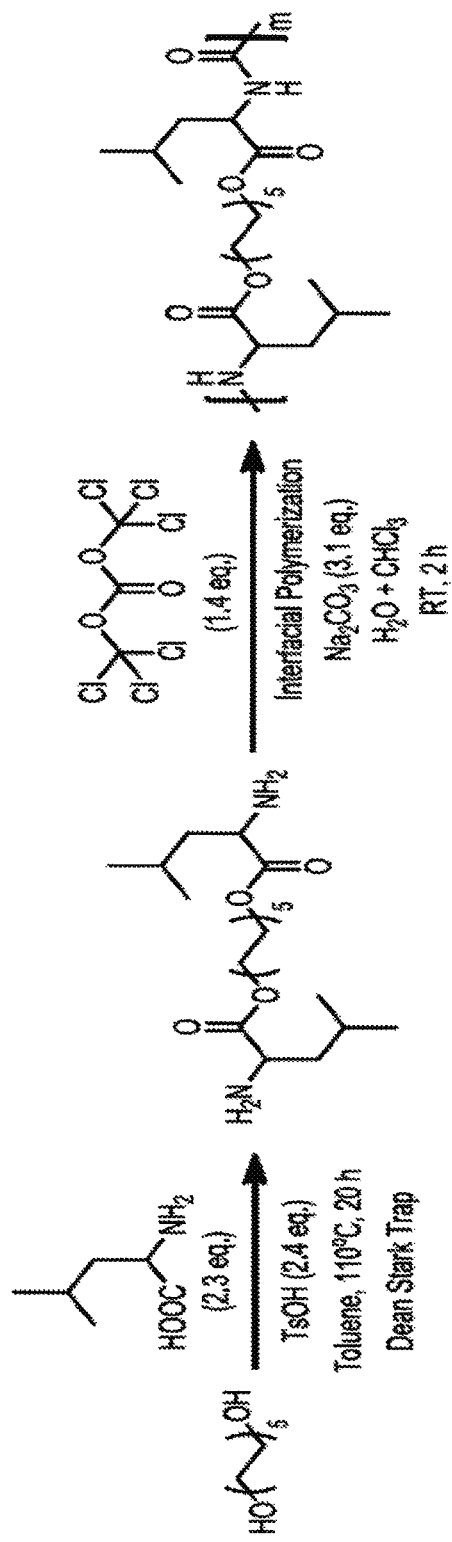
FIG. 1 provides a scheme of the two-step general synthetic route of amino acid-based poly(ester urea) (PEU). First 1,10-decanediol is condensed with 2 equivalents of amino acid (L-leucine) to obtain monomers. Here, p-toluene sulphonic acid (TsOH) protonated amine groups of the amino acid to prevent amidation and exchange reactions during the monomer synthesis. Following the deprotonation of amine groups of monomers, interfacial polycondensation with triphosgene yields the PEU polymer.

One or more embodiments are directed to an amino acid-based poly(ester urea) with amino acid residues selected from L-leucine, L-isoleucine, L-Valine or combinations thereof. The amino acid-based poly(ester urea) with amino acid residues selected from L-leucine, L-isoleucine, L-valine or combinations thereof may simply be referred to as the amino acid-based poly(ester urea). Advantageously, it has been found that amino acid-based poly(ester urea)s are biodegradable, resorbable with non-toxic hydrolysis byproducts, have tunable mechanic properties, synthetic flexibility, and the ability to be synthesized so that functional groups may be included. The amino acid-based poly(ester urea)s may find use in various biomaterials and devices.

The amino acid-based poly(ester urea)s particularly useful in preparing vascular grafts. While the amino acid-based poly(ester urea)s vascular grafts may have larger internal diameters, they are particularly suitable for use in vascular grafts with small internal diameters, such as less than 5 mm. In an animal study, the infra renal abdominal inferior vena cava was replaced in Severe Combined Immunodeficiency Mice with 0.6-0.7 mm inner diameter vascular grafts, and no acute thrombus and graft rupture were observed immediately after implanting in SCID mice in 24 hrs and the grafts continue perform well after 3-month implantation, indicating the grafts have good biocompatibility. Grafts continued to perform well after 12 months. Growth of new tissue in the lumen of the grafts was observed after 9 weeks and 12 months, showing the grafts have good regeneration potential.

In one or more embodiments, the amino acid-based poly (ester urea) comprises an amino acid residue selected from L-leucine, L-isoleucine, L-valine or combinations thereof; and a hydrocarbylene group; where the hydrocarbylene group is attached to the amino acid residue through an ester group. In one or more embodiments, the amino acid-based poly(ester urea) comprises amino acid residues attached to the amino acid-based poly(ester urea) through a urea group and an ester group, and a hydrocarbylene group attached to the amino acid-based poly(ester urea) through two ester groups.

Suitable hydrocarbylene groups include linear, branched or cyclic hydrocarbons with two valances. In one or more embodiment the hydrocarbylene groups have 1 to about 20 carbon atoms, in other embodiments about 5 to about 15 carbon atoms, and in still other embodiments about 10 to about 12 carbon atoms. Specific examples of hydrocarbylene groups include, but are not limited to methylene, ethylene, 1,3-propylene, 1,2-propylene, 1,4-butylene, 1,4-(2-methyl)butylene, 1,5-pentylene, 1,10-decylene, 1,11-undecylene, 1,12-dodecylene, 1,13-tridecylene, 1,14-tetradecylene, 1,15-pentadecylene, 1,16-hexadecylene, 1,17-heptadecylene, 1,18-octadecylene, 1,19-nonadecylene, and 1,20-eicosylene.

As noted above, the amino acid-based poly(ester urea) includes an amino acid residue selected from L-leucine, L-isoleucine, L-valine or combinations thereof. In one or more embodiments, the amino acid-based residues of the amino acid-based poly(ester urea) consist L-leucine, L-isoleucine, L-valine or combinations thereof. In other embodiments, the amino acid-based residues of the amino acid-based poly(ester urea) include other amino acids residues in addition to L-leucine, L-isoleucine, L-valine or combinations thereof. For purposes of this specification amino acids residues other than L-leucine, L-isoleucine, L-valine or combinations thereof in the amino acid-based poly(ester urea) may be referred to as second amino acid residues. In one or more embodiments, the amino acid-based poly(ester urea) further includes a second amino acid residue selected from proteinogenic amino acids and non-proteinogenic amino acids.

Proteinogenic amino acids include those amino acids that are incorporated into proteins during translation. Specific examples of proteinogenic amino acids include L-Alanine, L-Arginine, L-Asparagine, L-Aspartic acid, L-Cysteine, L-Glutamic acid, L-Glutamine, Glycine, L-Histidine, L-Isoleucine, L-Leucine, L-Lysine, L-Methionine, L-Phenylalanine, L-Proline, L-Serine, L-Threonine, L-Tryptophan, L-Tyrosine, and L-Valine, L-Selenocysteine, and L-Pyrrolysine.

Non-proteinogenic amino acids include those amino acids no coded for genetically. They may be prepared, for example, by post-translational modification. Also included in non-proteinogenic amino acids are those amino acids prepared synthetically by modifying or functionalizing an amino acid. Specific examples of functionalized amino acids may be found in PCT/US14/58264, which is incorporated herein by reference.

In one or more embodiments, the amino acid-based poly (ester urea) includes a second amino acid residue is defined by the formula:

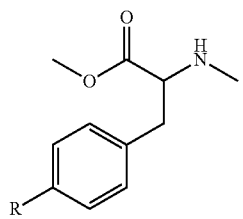

where R is a pendent functional group. An example of a suitable pendant functional group includes an oxygen atom connected to a alkyl or aryl group containing an alkyne group, an alkene group, an azide group, a benzyl protected phenol group, a ketone group or a strained cyclooctyne.

In one or more embodiments the amino acid-based poly (ester urea) comprises the following formula:

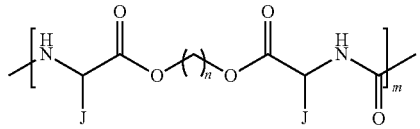

where each J is individually an L-leucine, L-isoleucine, or L-valine side chain, n is 1 to about 20 units, and m is about 10 to 500 units. In one or more embodiments n is about 5 to about 15 units, and in other embodiments n is about 10 to about 12 units. In one or more embodiments, were each J is an L-leucine side chain, the amino acid-based poly(ester urea) comprises the following formula:

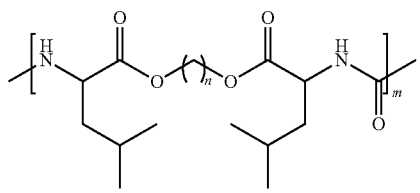

where n is about 1 to 20 units, and m is about 10 to 500 units. In one or more embodiments n is about 5 to about 15 units, and in other embodiments n is about 10 to about 12 units. In one or more embodiments, were each J is an L-isoleucine side chain, the amino acid-based poly(ester urea) comprises the following formula:

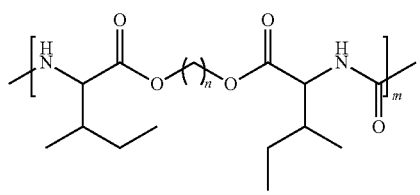

where n is about 1 to 20 units, and m is about 10 to 500 units. In one or more embodiments n is about 5 to about 15 units, and in other embodiments n is about 10 to about 12 units. In one or more embodiments, were each J is an L-valine side chain, the amino acid-based poly(ester urea) comprises the following formula:

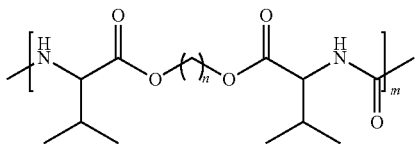

where n is about 1 to 20 units, and m is about 10 to 500 units. In one or more embodiments n is about 5 to about 15 units, and in other embodiments n is about 10 to about 12 units.

In one or more embodiments, were the amino add-based poly(ester urea) includes a second amino acid residue, the amino acid-based poly(ester urea) comprises the following formula:

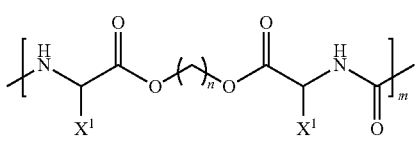

where each $X^1$ is individually an Leucine, L-isoleucine, L-valine, proteinogenic amino acid or non-proteinogenic amino acid side chain with the proviso that at least one $X^1$ is selected from L-leucine, L-isoleucine, or L-valine, n is 1 to about 20 units, and m is about 10 to 500 units. In one or more embodiments n is about 5 to about 15 units, and in other embodiments n is about 10 to about 12 units. In certain embodiments, were the amino acid based poly(ester urea) includes a second amino acid residue, the amino acid-based poly(ester urea) comprises the following formula:

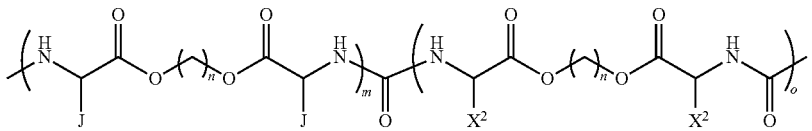

where each J is individually a L-leucine, L-isoleucine, or L-valine side chain, each $X^2$ is individually a proteinogenic amino acids or non-proteinogenic amino acid side chain, each n is individually about 1 to 20 units, and each m and o are individually about 10 to 500 units. In one or more embodiments n is about 5 to about 15 units, and in other embodiments n is about 10 to about 12 units. In certain embodiments, one or more of the $X^1$ or $X^2$ groups is a proteinogenic amino acids or non-proteinogenic amino acid side chain defined by the formula:

where R is a pendent fu anal group. A noted above, an example of a suitable pendant functional group includes an oxygen atom connected to a alkyl or aryl group containing an alkyne group, an alkene group, an azide group, a benzyl protected phenol group, a ketone group or a strained cyclooctyne.

The amino acid-based poly(ester urea)s may be characterized by the weight average molecular mass (Mw). The Mw may be determined by size exclusion chromatography. In one or more embodiments, the weight average molecular mass of the amino acid-based poly(ester urea) is from about 3,000 to about 300,000, in other embodiments from about 3,000 to about 100,000, in other embodiments from about 3,000 to about 50,000, and in other embodiments the average molecular mass is approximately 100,000 Da.

The amino acid-based poly(ester urea)s may be characterized by molecular mass distribution (Mw/Mn). In one or more embodiment, the Mw/Mn of the amino acid-based poly(ester urea) is from about 1.3 to about 3.5, in other embodiments from about 1.5 to about 3.0, in other embodiments from about 1.3 to about 2.5 in other embodiments, from about 1.3 to about 2.0, and in other embodiments from about 1.3 to about 1.6.

The amino acid-based poly(ester urea)s may be characterized by thermal decomposition temperature (Td). In one or more embodiments, the Td of the amino acid-based poly(ester urea) is from about 274° C. to about 277° C.

In one or more embodiments, the amino acid-based poly(ester urea) may be prepared first reacting L-leucine, L-isoleucine, L-valine or a combinations thereof with a diol to produce an amino acid-based monomer. In certain embodiments, where the amino acid-based poly(ester urea) includes a second amino acid residue selected from proteinogenic amino acids and non-proteinogenic amino acids, the second amino acid may be reacted with a diol along with the L-leucine, L-isoleucine, L-valine or combinations thereof or separate amino acid based monomer may be prepared with a second amino acid. The amino acid-based monomer may then be reacted with a phosgene or triphosgene to produce an amino acid-based poly(ester urea). Methods of synthesizing amino acid-based poly(ester urea)s may be found in PCT/US14/58264, which is incorporated herein by reference.

In one or more embodiments, the amino acid-based monomer for forming the amino acid-based poly(ester ureas) may be prepared by dissolving an amino acid selected from L-leucine, L-isoleucine, L-valine or combinations thereof (optionally with a second amino acid residue selected from proteinogenic amino acids and non-proteinogenic amino acids) in a suitable solvent and reacting the amino acid with a diol to produce an amino acid-based monomer. In one or more embodiments, the amine group of the amino acid may be protected before reaction with the diol. Surprisingly it has been found that amino acid-based poly(ester urea) prepared from diols with more than 10 carbons have reduced mechanical properties.

Suitable diols include diols with linear, branched or cyclic hydrocarbon groups. In one or more embodiment the diols have 1 to about 20 carbon atoms, in other embodiments about 5 to about 15 carbon atoms, and in still other embodiments about 10 to about 12 carbon atoms. Specific examples of diols include, but are not limited to, methylene glycol, ethylene glycol, propane-1,3-diol, propane-1,2-diol, butane-1,4-diol, (2-methyl)butane-1,4-diol, pentane-1,5-diol, decane-1,10-diol, undecane-1,11-diol, dodecane-1,12-diol, tridecane-1,13-diol, tetradecane-1,14-diol, pentadecane-1,15-diol, hexadecane-1,16-diol, heptadecane-1,17-diol, octadecane-1,18-diol, nonadecane-1,19-diol, and eicosane-1,20-diol.

In one or more embodiments, the amino acid-based poly(ester urea) may be prepared from the amino acid-based monomer by dissolving an amino acid-based monomer and a base selected from the group consisting of sodium carbonate, or potassium carbonate and combinations thereof in an aqueous solution; reducing the temperature of the solution to a temperature of from about −5° C. to about 5° C.; adding a solution comprising triphosgene or phosgene and a suitable organic solvent to the solution forming an interfacial mixture having an organic phase and an aqueous phase; separating the organic and aqueous phases of the interfacial mixture of and collecting and purifying said organic phase.

Amino acid-based poly(ester urea)s may be formed into a wide variety of 3-dimensional structures including, without limitation, tissue scaffolds, nanofibers, microfibers, coatings, and films. In one or more embodiments, 3-dimensional structures may be formed from the amino acid-based poly(ester urea)s using techniques such as blow molding, injection molding, extrusion, melt extrusion, 3-D printing, or electrospinning. The amino acid-based poly(ester ureas) may be soluble in polar organic solvents. Suitable polar organic solvents include, but are not limited to, N,N-dimethylformamide (DMF), dimethyl sulfoxide (DMSO), N-methyl-2-pyrrolidone (NMP), and hexafluoroisopropanol (HFIP). The solubility properties provide access to a number of approaches for solution processing methods for 3-dimensional structures of amino acid-based poly(ester urea)s, including solution casting, spinning coating and electrospinning, dip coating, and spray drying. Generally, when preparing 3-dimensional structures from amino acid-based poly(ester urea)s care should be taken so that the polymer is not heated beyond its thermal decomposition temperature.

In one or more embodiments, the amino acid-based poly(ester urea)s may be formed into fibers by any of the numerous methods known in that art for that purpose. Suitable methods include, but are not limited to electrospinning, melt blowing, blow spinning, centrifugal spinning, rotary jet spinning and Nanofibers by Gas Jet (NGJ) (see e.g. U.S. Pat. Nos. 6,382,526, 6,520,425, and 6,695,992, which are incorporated herein by reference in their entirety). In one or more embodiments, the amino acid-based poly(ester urea)s may be formed into fibers of various sizes obtained via electrospinning of polymer solutions or from the melt. One advantage of using electrospun fibers is that the physical and dimensional properties of fiber matrices can be tuned precisely. As those of skill in the art will appreciate, fiber diameter, alignment, surface-to-volume ratio, and porosity can be controlled in the electrospinning process.

Figure 6:
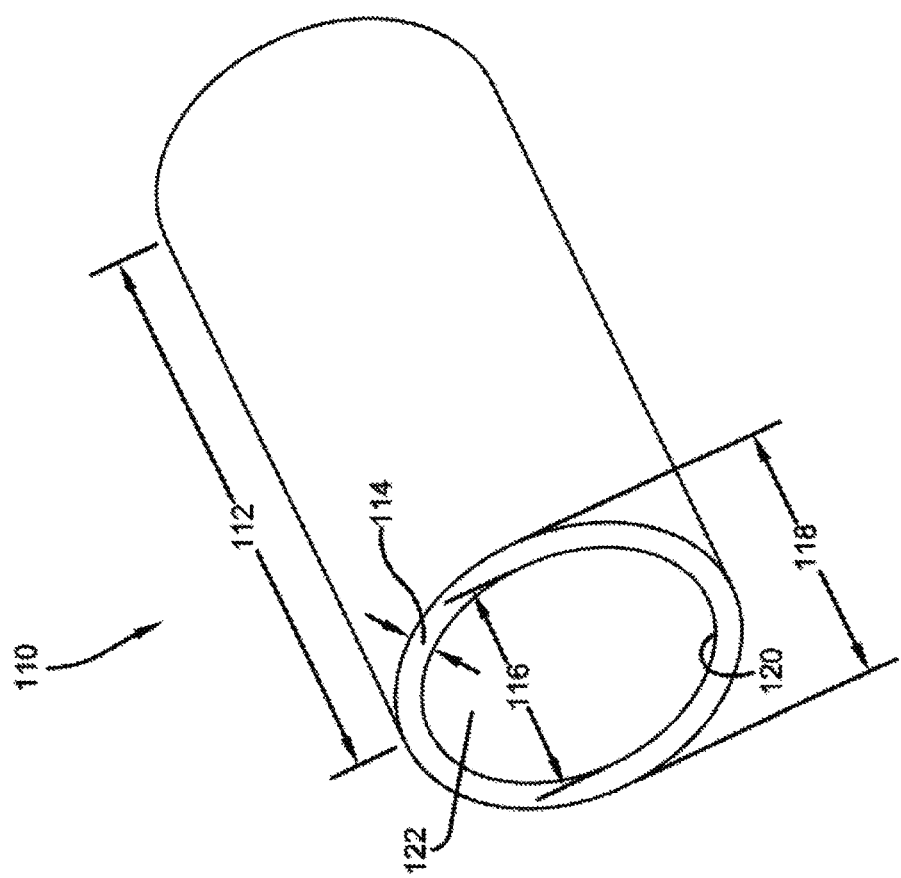
FIG. 6 provides a vascular graft according to one or more embodiments.

In one or more embodiments, the amino acid-based poly(ester urea) vascular graft comprising a tubular structure comprising an amino acid-based poly(ester urea) with amino acid residues selected from L-leucine, L-isoleucine, L-valine or combinations thereof. With reference to FIG. 6, vascular grafts may prepared from amino acid-based poly(ester urea)s may have the tubular structure 110. The tubular structure 110 has length 112, which is typically, but not necessarily always, the longest dimension. The tubular structure 110 has a wall 120 with a wall thickness 114. The tubular structure 110 also has a hollow interior 122 with an internal diameter 116. The tubular structure 110 also has a total diameter 118.

In one or more embodiments, the vascular graft has an internal diameter of about 0.5 mm to about 100 mm, in other embodiments the vascular graft has an internal diameter of about 0.5 mm to about 20 mm. Due to the biocompatibility of the amino acid-based poly(ester urea)s, vascular grafts prepared from amino acid-based poly(ester urea)s may be suitable for use with internal diameters less than 5 mm. In one or more embodiments, the vascular graft has an internal diameter of less than 5 mm. In one or more embodiments, the vascular graft has an internal diameter of about 0.5 mm to about 5 mm, in other embodiments of about 1 mm to about 4 mm, in other embodiments of about 2 mm to about 3 mm.

While the length of the vascular graft required may be determined by those skilled in the art based upon the location in a patient or animal where a graft is required, suitable vascular grafts may have a length of about 0.5 cm to about 5 cm. In one or more embodiments, the vascular graft has a wall thickness of about 0.05 mm to about 0.5 mm.

As noted above, the amino acid-based poly(ester urea)s particularly useful in preparing vascular grafts. In one or more embodiments, an amino acid-based poly(ester urea) vascular graft may be prepared by electrospinning an amino acid-based poly(ester urea) onto a spinning mandrel to produce a vascular graft. The amino acid-based poly(ester urea) vascular graft may be prepared by providing a charged solution of amino acid-based poly(ester urea); providing a grounded mandrel coated with a dissolvable coating; electrospinning the poly(ester urea) onto the dissolvable coating of the grounded mandrel to produce a tubular structure, dissolving the dissolvable coating; and removing the tubular structure from the mandrel. The tubular structure, or vascular graft, may optionally be dried after it is removed from the mandrel. Suitable methods of drying the vascular graft include, but are not limited to lyophilization.

With reference to FIG. 7, vascular grafts may be prepared from amino acid-based poly(ester urea)s using the electrospining. Electrospining apparatus 10 includes a reservoir 12 containing a polymer solution such as melted amino acid-based poly(ester urea) or amino acid-based poly(ester urea) dissolved in a solvent. The reservoir 12 may optionally be a syringe pump (not shown). The polymer solution in reservoir 12 is charged. The charged polymer solution exits the tip 14 to produce a fiber of amino acid-based poly(ester urea) 18. The tip 14 may optionally be moved back and forth to during the electrospining process. The fiber of amino acid-based poly(ester urea) 18 is attracted to the mandrel 16, which carries the opposite charge of the polymer solution. The charge on the mandrel 16 may be provided by terminal 30. The mandrel 16 is coated with a dissolvable coating 20. The mandrel 16 may be rotated clockwise or counter clockwise by the motor 22 as the fiber of amino acid-based poly(ester urea) 18 is applied to the mandrel 16 to produce a vascular graft. The mandrel has a diameter 26 and a dissolvable coating diameter 28, which is the total diameter including the dissolvable coating.

The speed of rotation, fiber width, fiber concentration (if in solution) and total time electrospinning may be tuned to control the wall thickness of the vascular graft. Suitable amino acid-based poly(ester urea) fiber diameters for preparing vascular graft may be about 50 nm to 5 about microns.

In one or more embodiments, the mandrel is rotated during the electrospinning step at a rate of about 20 rpm to about 5000 rpm, in other embodiments at a rate of about 50 rpm to about 1000 rpm, and in still other embodiments at a rate of about 75 rpm to about 500 rpm.

The dissolvable coating may be any coating that may dissolve in a solvent allowing the vascular graft to be released from the mandrel. Advantageously, it has been found that the use of a dissolvable coating on the mandrel allows the vascular graft to be released from the mandrel without rippling or disturbing the smooth interior surface of the vascular graft. Those skilled in the art will be able to select solvent and dissolvable coating pairs that will allow the vascular graft to be released from the mandrel.

Particularly useful dissolvable coatings are water soluble sugar. Water soluble sugars may be dissolved in water. Water soluble sugars are particularly advantageous, because vascular grafts may be introduced into patients, and any residual water soluble sugar form the preparation of a vascular graft has a minimal health risk. Suitable water soluble sugars include, but are not limited to sucrose, glucose, trehalose, and galactose.

Because the amino acid-based poly(ester urea) is applied to the diameter of the dissolvable coating on the mandrel determines the interior diameter of the vascular graft. In one or more embodiments the mandrel has a dissolvable coating diameter of about 0.5 mm to about 100 mm in other embodiments the mandrel has a dissolvable coating diameter of about 0.5 mm to about 20 mm. Due to the biocompatibility of the amino acid-based poly(ester urea)s, vascular grafts prepared from amino acid-based poly(ester urea)s may be suitable for use with diameters less than 5 mm. In one or more embodiments, the mandrel has a dissolvable coating diameter of less than 5 mm. In these or other embodiments, the mandrel has a dissolvable coating diameter of about 0.5 mm to about 5 mm.

EXAMPLES 1.1 Materials

Unless listed otherwise, all chemical solvents and reagents were purchased from Sigma-Aldrich or Alfa Aesar and used as received. Chloroform was dried with $CaH_2$ overnight and distilled before use. Cell culture and staining reagents were purchased from Invitrogen Corp or Lonza and used as received.

1.2 Polymer Synthesis and Characterization 1.2.1 Synthesis of Monomer. Di-p-toluenesulfonic acid salts of bis-L-leucine diester monomers were prepared as shown in FIG. 1. Briefly, to a 2 L three-neck round-bottom flask equipped with a Dean-Stark apparatus and a magnetic stirrer was added with diol (0.34 mol, 1.0 equiv), α-amino acids (0.78 mol, 2.3 equiv), p-toluenesulfonic acid (0.81 mol, 2.4 equiv), and toluene (1 L). The reaction mixture was refluxed for 48 h until no more water was produced. Then, it was cooled down to room temperature and toluene was evaporated under reduced pressure. The resulting monomers were recrystallized four times from water. The yield is about 75-90%. 1H NMR (500 MHz, DMSO-d6): 0.89 (m, 12H) 1.25 (m, 4H) 1.55-1.62 (m, 8H) 1.71 (m, 2H) 2.27 (s, 6H) 2.50 (m, DMSO) 3.30 (s, H2O) 3.96 (t, 2H) 4.13-4.17 (m, 4H) 7.08-7.11 (d, 4H) 7.45-7.47 (d, 4H) 8.23 (s, 6H). 13C NMR (500 MHz, DMSO-d6): 21.22, 22.36, 22.58, 24.26, 25.67, 28.34, 29.00, 29.30, 39.68-40.35 (DMSO-d6), 51.09, 66.09, 125.94, 128.50, 138.17, 145.94, 170.38.

1.2.2 Synthesis of Polymer

A general procedure of PEU polymer synthesis is like the following (FIG. 1): in brief, di-p-toluenesulfonic acid salt of bis-L-leucine diester monomers (0.038 mol, 1.0 equiv), sodium carbonate anhydrate (0.080 mol, 2.1 equiv), and distilled water (400 mL) were added into a 2 L three-neck round-bottom flask equipped with an overhead mechanical stirrer and a thermometer. The mixture was then heated with a warm water bath at 50° C. for 30 min. After then, the waterbath was removed and replaced with an ice-salt bath. When the inside temperature cooled to about 0° C., extra sodium carbonate (0.040 mol, 1.05 equiv) dissolved in 150 mL of distilled water was added to the mixture. Several minutes later, prepared triphosgene solution (0.013 mol, 1.05/3 equiv.) dissolved in 100 ml distilled chloroform was added to the reaction system as quickly as possible (<5 s) with fast mechanical stirring. The reaction was allowed to proceed for 30 min and then additional amount of triphosgene (0.003 mol, 0.25/3 equiv.) dissolved in 30 mL of distilled chloroform were added into the reaction system slowly in 30 mins. After the addition was completed, stirring was continued for 2 h. Later, the organic phase was precipitated into hot water, filtered and dried in vacuum to yield a white solid. The yield is about 85-95%. 1H NMR (500 MHz, DMSO-d6): 0.83-0.90 (m, 12H) 1.24 (m, 4H) 1.41-1.44 (m, 4H) 1.51-1.54 (t, 4H) 1.58-1.62 (m, 2H) 2.50 (DMSO) 3.28 (H2O) 3.97-4.01 (m, 4H) 4.11-4.14 (m, 2H) 6.26-6.28 (d, 2H). 13C NMR (500 MHz, DMSO-d6): 22.11, 23.06, 24.72, 25.70, 28.52, 29.04, 29.29, 39.17-40.84 (DMSO-d6), 41.43, 51.51, 64.57, 157.50, 173.84. FT-IR (cm-1): 1740 [—C(CO)—O—], 1640, 1555 [—NH—C(O)—NH—], 3355 [—NH—C(O)—NH—]; The polymers were then further characterized by size exclusion chromatography (SEC), thermogravimetric analysis (TGA), differential scanning calorimetry (DSC) and dynamic mechanical analysis (DMA). The characterization data summary of molecular weights and thermal properties of the polymers are listed in Table 1.

TABLE 1

Characterization Data Summary of the 1,10-decanediol and L-Leucine-based Poly(ester urea) (P(1-LEU-10)).

| Samples | Mw (g/mol) | Mn (g/mol) | PDI | Td/oC (TGA) | Tg/oC (DSC) | Tg/oC (DMA) |
|---|---|---|---|---|---|---|
| P(1-LEU-10) | 135,000 | 71,000 | 1.9 | 273 | 30 | 46 |

1.3 Graft Fabrication

Vascular grafts were fabricated by electrospinning using a 10 w % PEU polymer solution in hexafluoroisopropanol (HFIP). The electrospinning set-up included a syringe pump, a high voltage supply, and a rotating mandrel. A 10 kV positive voltage was applied to the polymer solution by the power supply. The polymer solution was drawn through a 23 gauge blunt tip needle at a constant flow rate of 1 mL/h. Polymer fibers were then collected on a grounded rotating mandrel mounted on a homemade stand. The collecting mandrel was a stainless steel rod with approximately 1 mm diameter. The collecting mandrel was pre-coated with sugar solution to make it easier to remove the graft from the mandrel. The distance between the syringe tip and the mandrel was set as 15 cm and the mandrel rotation rate was 100 rpm. To remove the graft from the mandrel, the graft together with the mandrel was soaked in DI water for one hour. When the thin layer of sugar was dissolved by water, the graft can be easily removed from the mandrel by gently pulling it from one direction. The obtained graft was then further dried by lyophilization and later stored in clean glass vial until use. Prior to implantation, the grafts were sterilized by ethylene oxide (ETO) for 24 hours.

1.4 Graft Characterization

The electrospun grafts were characterized using field emission scanning electron microscopy (FE-SEM; JSM-7401F, JEOL Ltd., Japan). Characterization included determining the average fiber diameter and average pore area. For each sample, ten SEM images were analyzed, and at least 50 fibers chosen randomly from across the image were manually measured on each image and analyzed using ImageJ software (NIH USA, 2008). Pore areas were also measured by a subjective approximation of surface pores from the SEM images (at least 20 measurements per image). Results are given as mean±standard deviation. For all of the measurements made from the SEM images, calibration of the ImageJ software was done with the scale bar on each image.

1.5 Biomechanical Evaluations

1.5.1 Tensile Properties

Uniaxial tensile testing of electrospun grafts was performed on six 1 mm inner diameter tubular specimens from six different electrospun grafts using an Instron 5567 universal tensile testing machine. After soaking the specimens in PBS for 24 h at 37° C., tensile properties were measured by clamping a 20 mm long graft in the tensile-testing machine and pulling the samples until failure. The gauge length was set as 10 mm, and the crosshead speed was set at 10 mm/min. Stress-strain data were reported using the Instron Bluehill software. The data were plotted using Origin 8.1 and the ultimate tensile strength, modulus, and strain at break were calculated. Results presented are average values for three individual measurements.

1.5.2 Suture Retention Strength

Suture retention testing was performed on six 1 mm inner diameter tubular specimens from six different electrospun grafts according to the procedure described in Section 8.8 of the American National Standards Institute (ANSI)/Association for the Advancement of Medical Instrumentation (AAMI) ANSI/AAMI VP20:1994 entitled "Cardiovascular Implants-Vascular Graft Prostheses": After soaking the grafts in PBS for 24 h at 37° C., one end of the graft was fixed to the stage clamp of the uniaxial tensile testing machine (Instron 5567, USA) and the other end was connected to another clamp by a loop of a common suture material (5-0 Prolene, Ethicon Inc.) placed 2 mm from the edge of the free end of the graft. The gauge length was set as 20 mm, and the crosshead speed was set at 150 mm/min until the suture ripped or the graft failed. Suture retention strength, which was defined as fracture strength, was recorded in Newton using the Instron Bluehill software.

1.5.3 Burst Pressure Strength

The burst pressure strength for the electrospun grafts was measured by increasing the pressure within the tubular vascular graft until failure occurred (in our case, the pressure level reached the limitation of the machine before graft failed). Luer-lock needle adapters with matching size of the testing grafts were inserted and fixed by superglue to both ends of the grafts. A pressure transducer catheter which connected to computer was attached to one end of the grafts via the luer-lock needle adapters. A 100 mL pressure syringe was attached to the other end of the grafts. The pressure was gradually increased until reaching the limitation of the machine and the pressure change was recorded on computer.

TABLE 2

Physical properties of the electrospun grafts.

| | Tensile testing (n = 6) | | | Suture retention strength (N) (n = 6) | Burst pressure (mm Hg) (n = 3) | Compliance (%) (n = 3) | Image analysis | |
|---|---|---|---|---|---|---|---|---|
| Samples | Ultimate tensile strength (MPa) | Elastic modulus (MPa) | Elongation at break (%) | | | | Fiber diameter (nm) | Pore area (um$^2$) |
| PEU grafts | 1.7 ± 0.2 | 1.8 ± 0.1 | 598 ± 26 | 8.7 ± 0.4 | >1000 | — | 422 ± 33 | 10 ± 4 |

1.6 Biological Activity Evaluations

For cell culture studies, PEU polymer was electrospun onto glass coverslips to form two-dimensional fiber structures. The PEU nanofiber covered glass coverslips were then placed into 12-well plates, gas sterilized by ethylene oxide for 24 h, and pre-soaked for 4 h in cell culture medium prior to seeding. Blank glass coverslips were used as control study. A-10 smooth muscle cells (A-10 SMCs) and human umbilical vein endothelial cells (HUVECs) between passage 10 and 14 were used and seeded directly on the surface of the glass coverslips at a density of 2×104 per well. The cell-seeded coverslips were incubated for 4 h to allow cells to adhere to the nanofibers before adding additional cell culture medium to the culture plate. Samples of separate studies were all done in triplicate to assure reproducibility of the results. A-10 SMCs were cultured with Dulbecco's Modified Eagle's Medium (DMEM) supplemented with 10% fetal bovine serum (FBS) and 1% penicillin and streptomycin. HUVECs were cultured with EGM™-2 Bulletkit™ (Lonza) with basal medium, growth factors, cytokines, and supplements special for endothelial cells. Both cell types were cultured at 37° C. in a humidified incubator containing 5% CO2 for scheduled time. The cell culture medium was changed every 48 hours.

1.6.1 Cell Viability and Proliferation Study

Cell viability and proliferation were evaluated after 1, 3 and 7 days of cell seeding using PrestoBlue assay. Upon entering a living cell, PrestoBlue® reagent is reduced from resazurin, a blue compound with no intrinsic fluorescent value, to resorufin which is red in color and highly fluorescent. Cell proliferation was assessed by the intensity of red color obtained, which was directly proportional to the metabolic activity of the cell population. At scheduled time points (day 1, 3, and 7), cell culture medium was removed. Cell seeded coverslips were transferred to empty 12-well culture plates and refilled by 1 mL of fresh cell medium containing 10% v/v of PrestoBlue. After 0.5 to 2 h of incubation at 37° C., 3×100 μL of medium was taken from each well to a 96-well plate and analyzed for fluorescence measurement. The fluorescence intensity was measured on a Synergy™ MX plate reader from BioTek at an excitation wavelength of 560 nm and an emission wavelength of 590 nm. The observed fluorescence intensity was then converted to cell numbers according to established calibration curves.

1.6.2 Cell Attachment and Spreading Study

To study cell attachment and spreading on the scaffold material, A-10 SMCs and HUVECs at a density of 2×104 per well were seeded directly on the surface of the PEU nanofiber covered glass coverslips in 12-well culture plates and were cultured for 48 h before fixation and immunostaining. For immunostaining studies, cells were first fixed by 3.7% paraformaldehyde in CS buffer for 10 min on dry block and then permeabilized with 0.5% TritonX-100 for 9 min. Excess formaldehyde was quenched with 0.05% sodium borohydride in PBS. 5% donkey serum in CS buffer was then added and the well plate was incubated at room temperature for 20 mins to block the non-specific binding activity. The actin filaments of the cytoskeleton were then stained with rhodamine phalloidin (1:200 dilution in PBS) for 1 h. After three time rinse with PBS, the nucleus was stained with DAPI (1:1000 dilution in PBS) for 20 mins and washed four times with PBS. Coverslips were mounted on microscope slides with mounting medium for fluorescence (Vector Laboratories Inc. Burlingame, Calif.) and sealed with nail enamel upon drying. Fluorescent pictures were taken using IX 81 microscope (Olympus, Center Valley, Pa.) with 10×, 20× and 40× objectives. Image J software was used to determine average cell number and cell area.

2. Results

2.1 Polymer Synthesis and Characterization

The current PEU polymers were prepared from L-leucine, 1,10-decanediol, and triphosgene by interfacial polymerization according to FIG. 1. L-leucine was chosen because of its bulky aliphatic side chain. Compared with amino acids with more rigid aromatic side chains (e.g. L-Phenylalanine), it will provide the resulting PEUs with more elasticity. The structures of the synthesized PEU monomer and polymer were confirmed by 1H NMR, 13C NMR and FT-IR spectroscopy, from which it could be seen that all the assigned peaks are expected from the monomer and polymer structures. The monomer and polymer were obtained with high purities. Furthermore, the molecular weight, molecular weight distribution and thermal properties of the resulting P(1-LEU-10) polymer were measured (Table 1). In this work, interfacial polymerization was chosen to prepare the PEU polymers since the solution polymerization approach generally produced relatively low molecular weight polymers not suitable for biomedical applications while interfacial polymerization allows the synthesis of linear polymers with high molecular weights. High molecular weight PEUs (Mw exceeding to 100K Da) with good fiber forming property were easily obtained in our study using interfacial polymerization. It is worth noted here that the molecular weights of PEUs that we synthesized are much higher than most PEUs or polymer with similar structure (e.g. poly(ester amides)) reported in the literatures, which is of great significance since sufficiently higher molecular weight PEUs that are capable of film, fiber and scaffold forming are required for their practical applications such as biomaterial scaffolds. Moreover, the degradation temperatures (Td) of the P(1-LEU-10) material is very high, indicating that this materials can be melt processed with limited impact of thermal degradation. These characteristics allow processing techniques such as molding and melt processing to be used to fabricate our scaffolds in addition to electrospining.

2.2 Scaffold Characterization

Figure 2A:
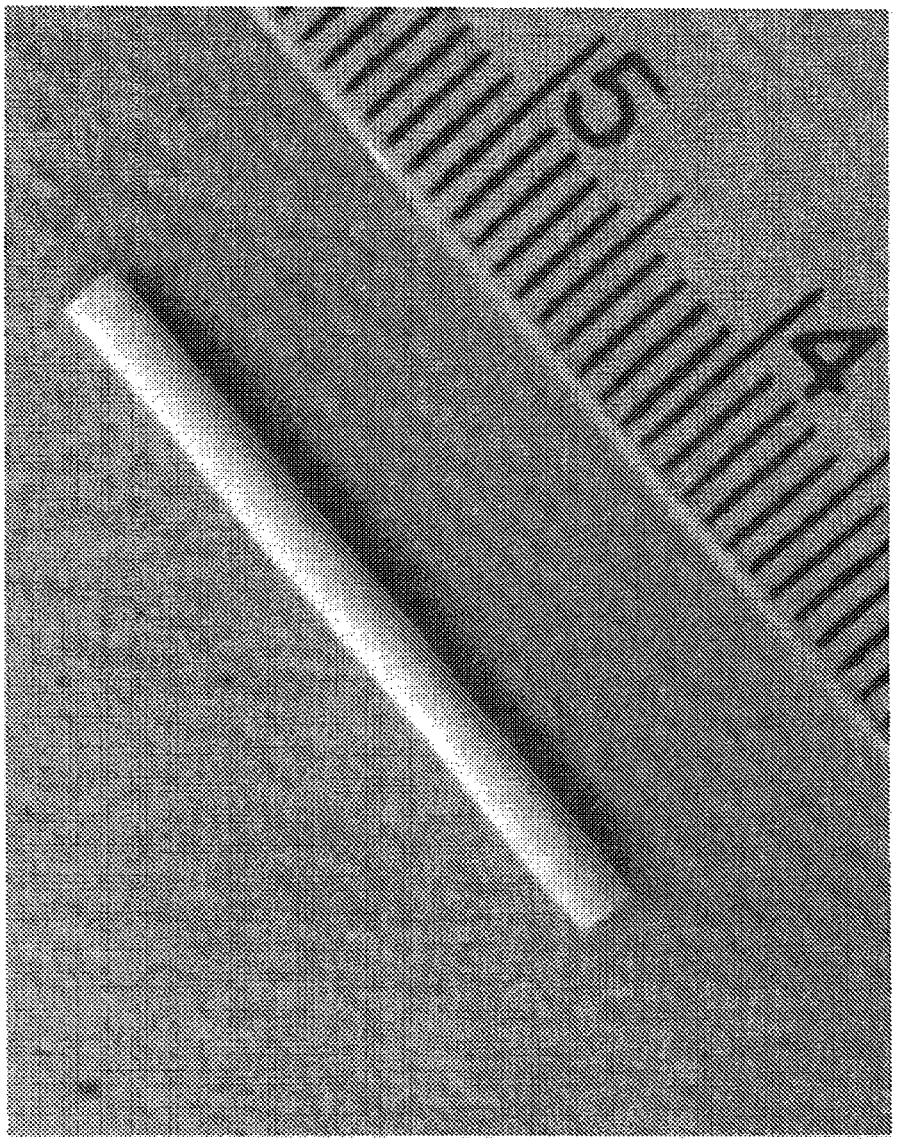
FIG. 2A provides an image of the gross appearance of a PEU based small diameter vascular graft.
Figure 2B:
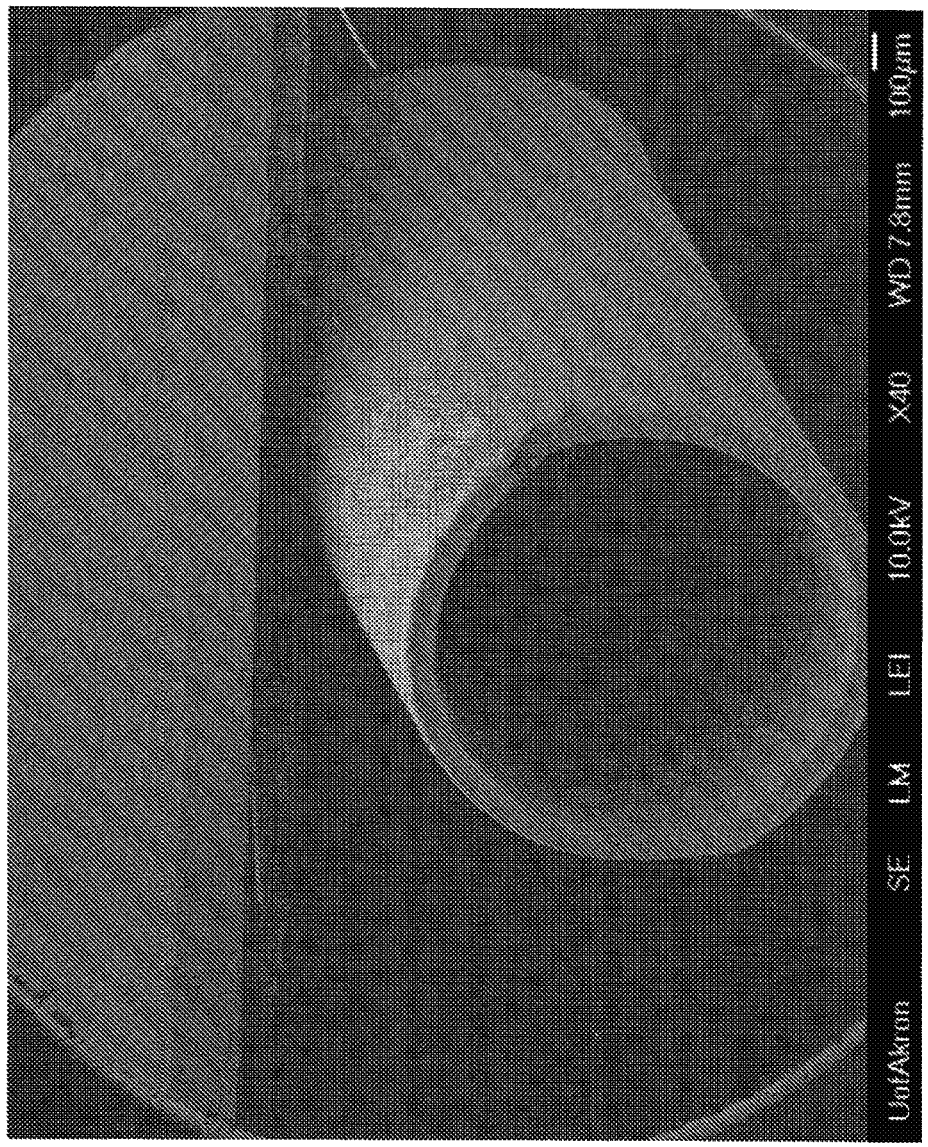
FIG. 2B provides an SEM image of the entire (×40 magnification) PEU based small diameter vascular grafts. Based on the SEM image analysis, the average fiber diameter and pore size are 422±33 nm and 10±4 um2, respectively.
Figure 2C:
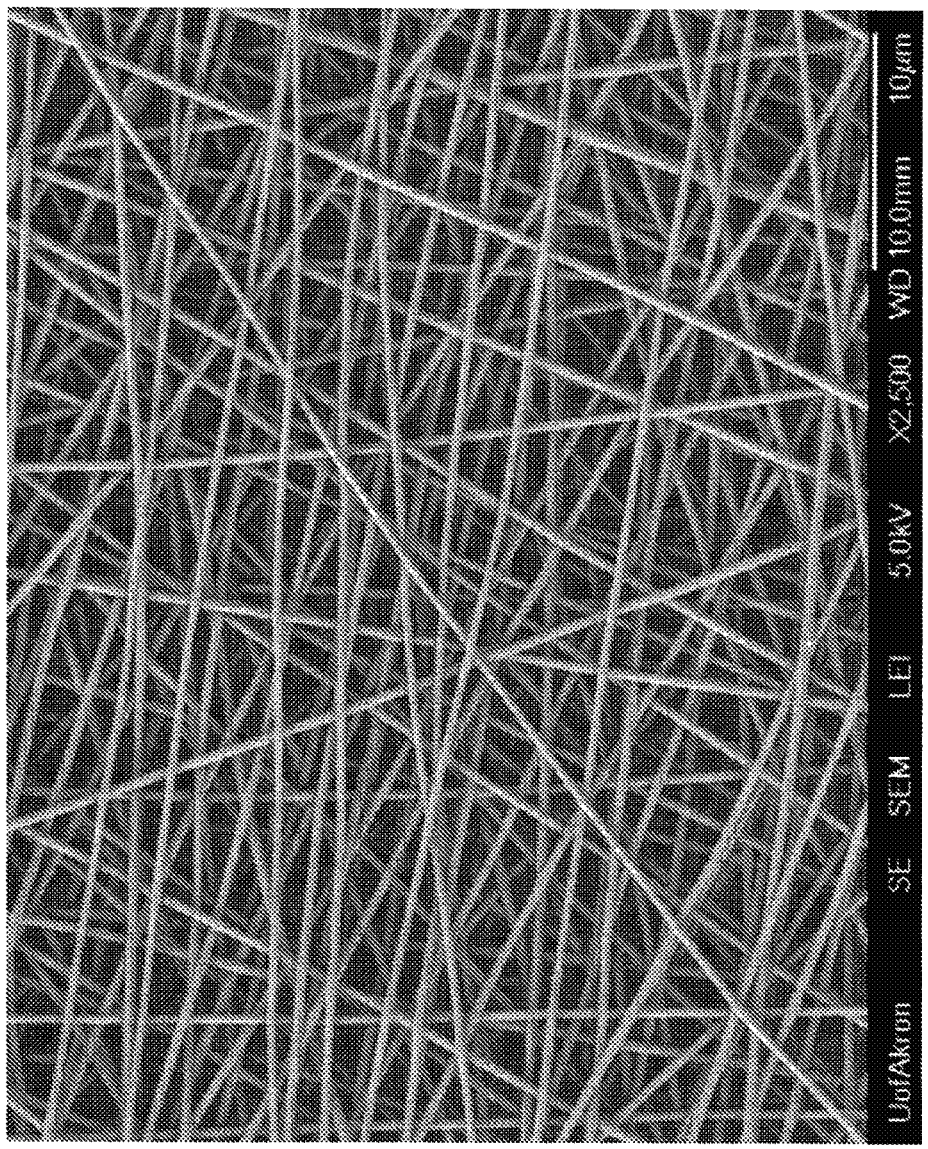
FIG. 2C provides an SEM image of the surface (×2.5 K magnification) of a PEU based small diameter vascular graft.
Figure 2D:
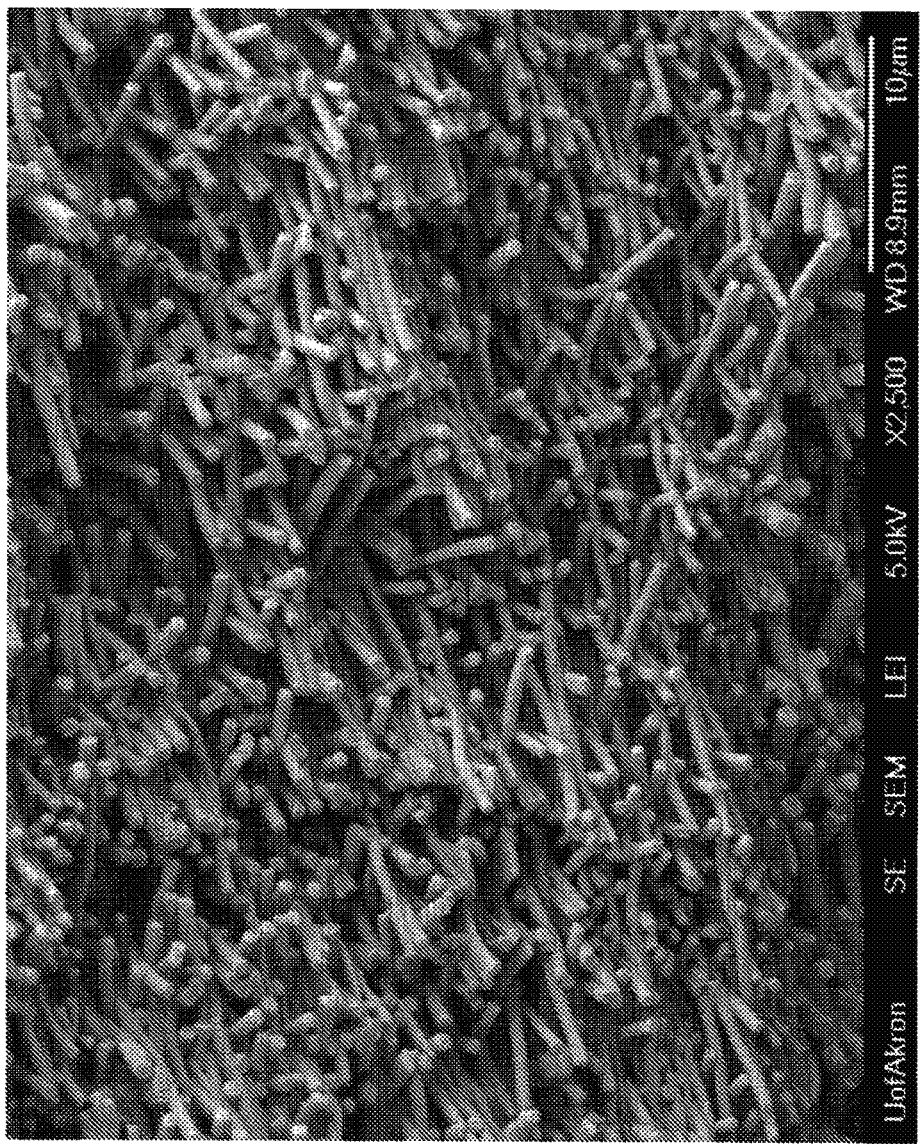

Electrospinning conditions (solution concentration, flow rate, voltage levels, and distance between the needle tip and the mandrel, etc.) were optimized in order to obtain uniform bead-free nanofibrous morphology before starting collection on rotating mandrel for graft fabrication. Graft scaffolds obtained were cut into 1 mm thick cross-sections and imaged on a field emission SEM (FE-SEM; JSM-7401F, JEOL Ltd., Japan). Fiber diameters at the outer surface and wall thickness were measured from high and low magnification SEM images. FIG. 2A shows a gross appearance of the whole graft tube. The grafts fabricated were generally about 3 cm in length and approximately 1 mm in inner diameter. FIG. 2B shows tilted view of the graft tube at low magnification SEM. High magnification SEM zoomed in the graft surface and cross-sectional area of the grafts were shown in FIGS. 2C and 2D. Randomly oriented fibers with smooth surface and well defined fiber morphology were observed. The averaged fiber diameter and pore area counted by ImageJ were 422±33 nm and 10±4 um2, respectively. Additionally, the wall thickness of the graft tubes, as determined from SEM images, was found proportionally increasing with the electrospinning collecting time, indicating that the wall thickness can well controlled by adjusting the electrospinning collecting time. The wall thicknesses of the tubes fabricated at different electrospinning collecting times were as follows: 94±17 um (t=30 min), 141±27 um (t=60 min), 254±18 um (t=90 min) and 305±18 um (t=120 min).

2.3 Biomechanical Properties of Scaffolds

The tensile properties, suture retention strength, and burst pressure were measured on all scaffolds to ensure that they possessed significant biomechanical properties to function as vascular grafts.

Figure 3:
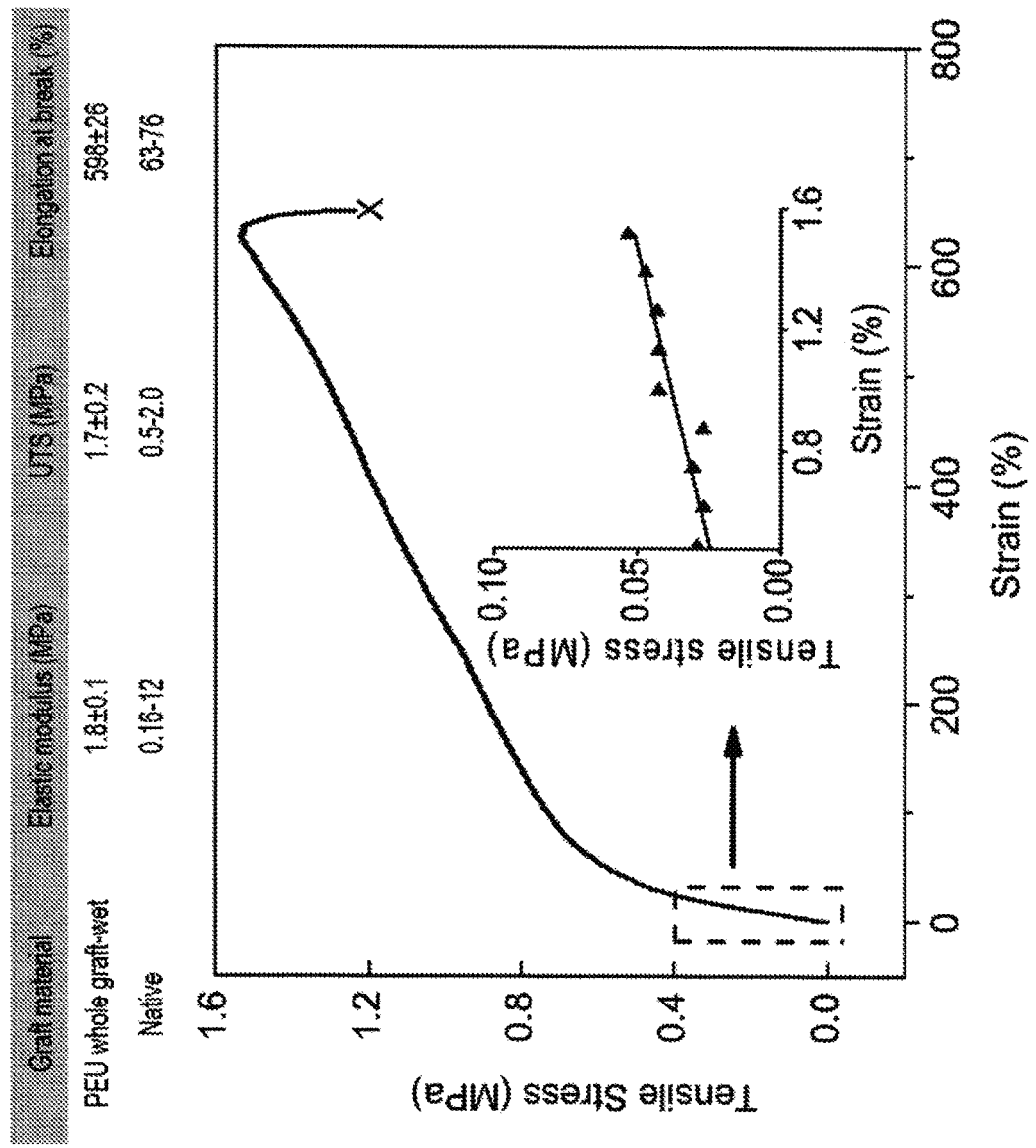
FIG. 3 provides a chart of the stress-strain curve of whole PEU graft in wet condition from uniaxial tensile testing. The elastic modulus and tensile properties of the PEU grafts were measured using an Instron 3365 universal materials testing machine. The gauge length was 10 mm and the crosshead speed was set at 10 mmmin-1. The elastic moduli of the grafts, ultimate tensile stress (UTS) and elongation at break (%) were obtained from the stress-strain curve. Results presented are average values for six individual measurements. The PEU grafts show comparable mechanical properties to native blood vessels. The elastic modulus and ultimate tensile stress of the PEU grafts fell into the range of native blood vessels.
Figure 4:
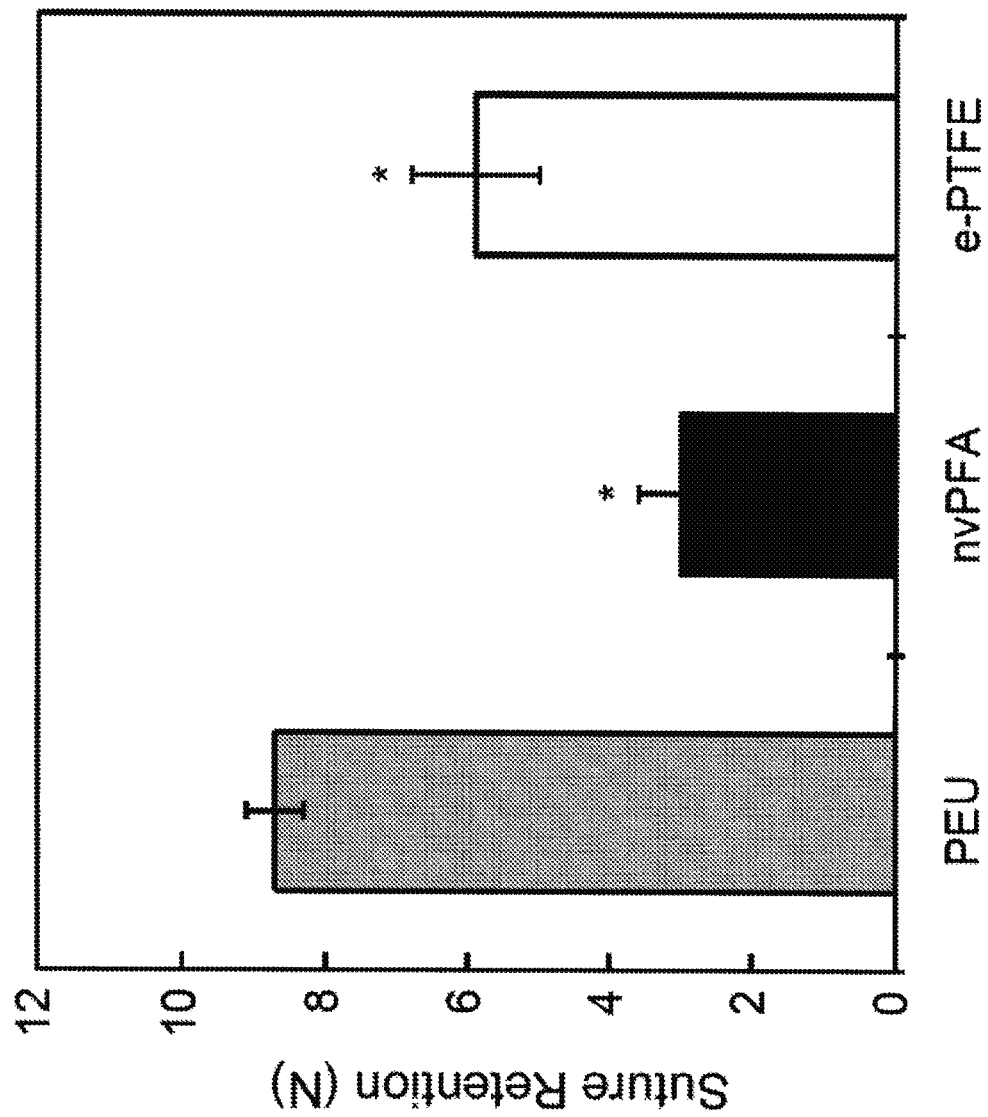
FIG. 4 provides a graph of the suture retention strength of whole PEU grafts with commercial 5-0 Prolene sutures. Compared to native and common used commercial grafts (suture retention of nvPFA=nonviable porcine femoral artery and commercial ePTFE grafts cited from papers (McClure, M. J.; Sell, S. A.; Simpson, D. G.; Walpoth, B. H.; Bowlin, G. L. Acta Biomaterialia 2010, 6, 2422-2433) were referenced as controls), the PEU grafts show adequate suture retention strength for implantation.

The tensile properties of the graft scaffolds were studied by uniaxial tensile testing of the whole graft using an Instron 5567 universal tensile testing machine. Based on stress-strain curve of the whole electrospun grafts (FIG. 3), the ultimate tensile strength (UTS), elongation at break, and elastic modulus of the grafts were obtained. The graft scaffolds showed averaged elastic modulus of 1.8±0.1 MPa, ultimate tensile strength of 1.7±0.2 MPa and elongation at break of 598±26%. Here, it is noted that that the elastic modulus and ultimate tensile strength of the PEU grafts fell within the range of the native blood vessels, which is of great significance, since the close the mechanical properties of grafts come to that of native blood vessels, the less the chance of graft failure due to mechanical property mismatch. In addition, this matching of mechanical properties may aid in reducing compliance mismatch as well.

Suture retention strength is essential to evaluate the material for resisting the tension during implantation and it directly relates to the success of the graft implantation procedure. Results analysis as determined by the ultimate tensile strength test demonstrated the electrospun PEU grafts show sufficiently high enough suture retention strength (8.7±0.4 N). Compared to suture strength of native artery (nonviable porcine femoral artery, nvPFA, 2.31-3.51 N) and commonly used vascular graft material (ePTFE, 4.91-6.67 N), as referred from previous published papers, the electrospun PEU grafts showed more than adequate strength for suturing during implantation. Also, there are other previous works reported it is generally accepted to be greater than 2.0 N.

Burst pressure identified as the maximum pressure that the scaffolds could endure before failure is a crucial factor to determine whether the scaffold material is strong enough to endure physiologic forces and avoid blood leakage. In our case, the limitation of the burst pressure testing machine is 1000 mmHg. As the pressure inside the grafts with continuous water flow increased gradually until it reached the limitation of the machine, the PEU electrospun grafts did not break even after we held the pressure at 1000 mmHg for 30 mins and no leakage was observed either. Though technically, the testing result can't be called burst pressure since we did not break the grafts due to the limitation of the machine and can't compare with that of native artery and common used vascular grafts, the current results still demonstrated that the PEU grafts possess excellent physical strength and can be developed as substitutes for native blood vessels since the blood pressure is generally less than 200 mm Hg for human beings.

2.4 Biological Activity Evaluations

There is little evidence regarding the ability of PEUs to support vascular cell attachment and proliferation, which is a first requirement for vascular tissue engineering applications. In order to evaluate to what extent the current PEU materials support the attachment and spreading of vascular cells, A-10 SMCs and HUVECs were seeded on positive control glass coverslips and electrospun PEU covered glass coverslips, both of which are two-dimensional (2D) surfaces. After being cultured for up to 48 h, labeling for F-actin and DNA were used to examine cellular morphology. Both A-10 SMCs and HUVECs were well attached and spread on the 2D surface with abundant and aligned F-actin expression, suggesting that the PEU nanofibers are able to support vascular cell adhesion and spreading in vitro. Since cell adhesion and spreading are the first events that dictate the subsequent cellular responses such as proliferation, migration and matrix deposition, it is important that the PEU nanofibers were able to promote these initial events.

Figure 5:
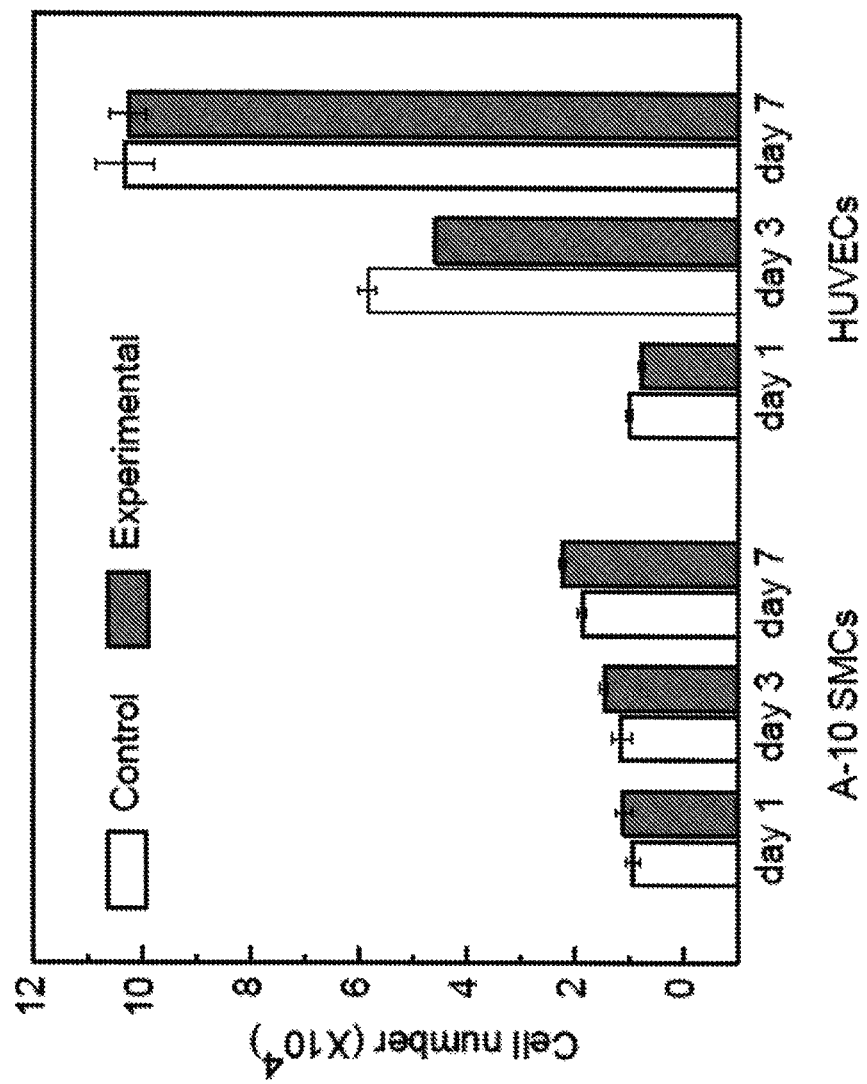
FIG. 5 provides a chart of the cell proliferation of A-10 smooth muscle cells (A-10 SMCs) and human umbilical vein cells (HUVECs) cultured in direct contact with electrospun PEU nanofibers after 1, 3 and 7 days of cell seeding, as determined by PrestoBlue assay. Blank glass coverslips are used for all positive controls. The results indicate the PEU nanofibers are able to support proliferation of A-10 SMCs and HUVECs in vitro.

The growth of vascular cells on the nanofibrous scaffolds is another critical issue for their clinical applications. The evaluation of proliferation of A-10 SMCs and HUVECs on electrospun PEU nanofiber in vitro can provide initial confirmation of the utility of the scaffolds. The growth profiles of A-10 SMCs and HUVECs cultured on the positive control glass coverslips and electrospun PEU covered glass coverslips were measured over a seven-day time course. As shown in FIG. 5, the vascular cells continued to increase in number over the time interval examined on both positive controls and electrospun PEU, indicating that the PEU nanofibers are able to support vascular cell proliferation without producing toxic effects for at least 7 days in vitro.

While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

What is claimed is:

1. An amino acid-based poly(ester urea) comprising
a first amino acid residue selected from the group consisting of L-leucine, isoleucine, L-valine and combinations thereof attached to a hydrocarbylene group having from 10 to 12 carbon atoms through an ester group; and
a second amino acid residue defined by the formula:

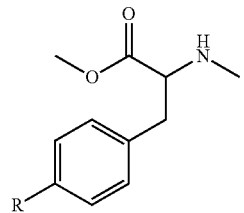

where R is a pendent functional group, wherein said second amino acid residue is attached to a hydrocarbylene group having from 10 to 12 carbon atoms through an ester group.

2. The amino acid-based poly(ester urea) of claim 1, where the pendent functional group is an oxygen atom connected to a alkyl or aryl group containing an alkyne group, an alkene group, an azide group, a benzyl protected phenol group, a ketone group or a strained cyclooctyne.

3. The amino acid-based poly(ester urea) of claim 1, where the amino acid-based poly(ester urea) comprises the following formula:

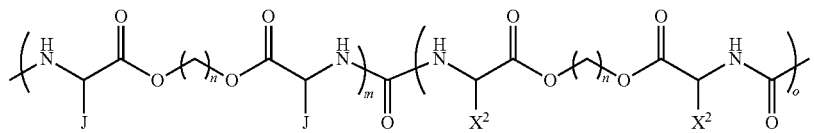

where each J is individually a L-leucine, L-isoleucine, or L-valine side chain, at least one $X^2$ is a proteinogenic amino add or non-proteinogenic amino acid side chain defined by the formula:

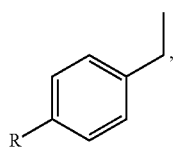

where R is a pendent functional group; each n is individually about 10 to 12 units; m is from about 10 to about 500 units; and o is from about 10 to about 500 units.

4. An amino acid-based poly(ester urea) vascular graft having a tubular structure comprising an amino acid-based poly(ester urea), said amino acid-based poly(ester urea) comprising:
a first amino acid residue selected from L-leucine, L-isoleucine, L-valine or combinations thereof attached to a hydrocarbylene group having from 10 to 12 carbon atoms through an ester group; and
a second amino acid residue defined by the formula:

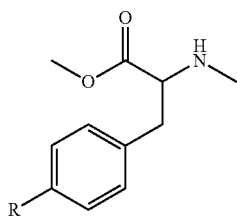

where R is a pendent functional group, wherein said second amino acid residue is attached to a hydrocarbylene group having from 10 to 12 carbon atoms through an ester group.

5. The poly(ester urea) vascular graft of claim 4, where the amino acid-based poly(ester urea) is defined by the following formula:

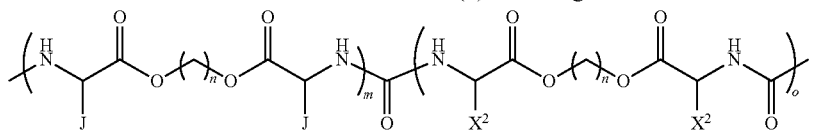

where each J is individually a L-leucine, L-isoleucine, or L-valine side chain, each n is about 10 to 23 units, m is from about 10 to about 500 units; o is about 10 to about 500 units; at least one $X^2$ is a proteinogenic amino acid or non-proteinogenic amino acid side chain defined by the formula:

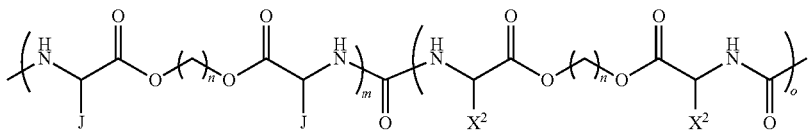

where R is a pendent functional group.

6. The poly(ester urea) vascular graft of claim 5, where R is a pendent functional group comprising an oxygen atom connected to an alkyl or aryl group containing an alkyne group, an alkene group, an azide group, a benzyl protected phenol group, a ketone group or a strained cyclooctyne.

7. The poly(ester urea) vascular graft of claim 4, There the poly(ester urea) is electrospun.

8. The poly(ester urea) vascular graft of claim 4, where the vascular graft has an internal diameter of about 0.05 mm to about 20 mm.

9. A method of preparing an amino acid-based poly(ester urea) vascular graft comprising
(i) providing a charged solution of amino acid-based poly(ester urea) wherein said amino acid-based poly (ester urea) is defined by the following formula;

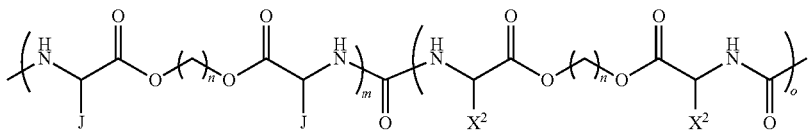

where each J is individually a L-leucine, L-isoleucine, or L-valine side chain, at least one $X^2$ is a proteinogenic amino acid or non-proteinogenic amino acid side chain defined by the formula:

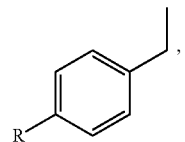

where R is a pendent functional group; each n is individually about 10 to 12 units; m is from about 10 to about 500 units; and o is from about 10 to about 500 units;
(ii) providing a grounded mandrel coated with a dissolvable coating;
(iii) electrospinning the charged solution of amino acid-based poly(ester urea) onto the dissolvable coating of the grounded mandrel to produce a tubular structure,
(iv) dissolving the dissolvable coating; and
(v) removing the tubular structure from the mandrel.

10. The method of claim 9, where the dissolvable coating is a water soluble sugar.

11. The method of claim 9, wherein said pendent functional group (R) is an oxygen atom connected to a alkyl or aryl group containing an alkyne group, an alkene group, an azide group, a benzyl protected phenol group, a ketone group or a strained cyclooctyne.

* * * * *